US010130442B2

(12) United States Patent
Dor et al.

(10) Patent No.: US 10,130,442 B2
(45) Date of Patent: Nov. 20, 2018

(54) INTERCHANGEABLE TAG AND ATTACHMENT

(71) Applicant: HALDOR ADVANCED TECHNOLOGIES LTD, Hod HaSharon (IL)

(72) Inventors: Guy Dor, Rosh Haayn (IL); Dan Zeeli, North York (CA); Ilan Kadosh-Tamari, Ramat Hasharon (IL)

(73) Assignee: HALDOR ADVANCED TECHNOLOGIES LTD, Hod Hasharon (IL)

( * ) Notice: Subject to any disclaimer, the term of this patent is extended or adjusted under 35 U.S.C. 154(b) by 0 days.

(21) Appl. No.: 15/562,443

(22) PCT Filed: Mar. 29, 2016

(86) PCT No.: PCT/IL2016/050334
§ 371 (c)(1),
(2) Date: Sep. 28, 2017

(87) PCT Pub. No.: WO2016/157180
PCT Pub. Date: Oct. 6, 2016

(65) Prior Publication Data

US 2018/0085187 A1 Mar. 29, 2018

Related U.S. Application Data

(60) Provisional application No. 62/141,295, filed on Apr. 1, 2015.

(51) Int. Cl.
*A61B 90/98* (2016.01)
*G06K 19/04* (2006.01)
(Continued)

(52) U.S. Cl.
CPC .............. *A61B 90/98* (2016.02); *A61B 90/90* (2016.02); *G06K 19/041* (2013.01); *G06K 19/07758* (2013.01); *G06K 2017/009* (2013.01)

(58) Field of Classification Search
CPC ...... A61B 90/90; A61B 90/98; G06K 19/041; G06K 19/07749; G06K 19/07758
(Continued)

(56) References Cited

U.S. PATENT DOCUMENTS 6,239,737 B1 5/2001 Black
7,859,416 B2 * 12/2010 Tuttle ............... G06K 19/07758 235/492
(Continued)

FOREIGN PATENT DOCUMENTS

CA 2 886 005 A1 3/2014
WO 2006/086603 A2 8/2006
(Continued)

*Primary Examiner* — Adnan Aziz
(74) *Attorney, Agent, or Firm* — Soroker Agmon Nordman

(57) ABSTRACT

An interchangeable tag for attaching to an item for automatically identifying the item, including: a base with a small footprint for attaching to the item at a first end of the base; an identification head with a larger footprint that is attached to the item by the base at a second end of the base; wherein the identification head wirelessly accepts communication queries and transmits identification information related to the item; and wherein the base is attached to the tool by a technological process that requires use of an attachment tool by a skilled user and the identification head is attached to the base after attaching it to the item by a simple process that is performed without requiring an attachment tool.

15 Claims, 7 Drawing Sheets

100
120
130
110
160
150
140

(51) Int. Cl.

| | |
|---|---|
| ***G06K 19/077*** | (2006.01) |
| ***A61B 90/90*** | (2016.01) |
| *G06K 17/00* | (2006.01) |

(58) Field of Classification Search

USPC .................................. 340/572.1–572.8, 10.1

See application file for complete search history.

(56) References Cited

U.S. PATENT DOCUMENTS

| | | | | |
|---|---|---|---|---|
| 7,887,559 | B2 * | 2/2011 | Deng | A61B 17/32002 15/21.1 |
| 8,033,181 | B2 * | 10/2011 | Kibblewhite | G01L 1/255 73/761 |
| 8,087,584 | B2 * | 1/2012 | Grimard | A61B 17/1659 235/380 |
| 8,726,911 | B2 * | 5/2014 | Blair | A61B 19/44 128/899 |
| 8,937,544 | B2 * | 1/2015 | Rigsby | A61B 17/7001 235/385 |
| 9,119,667 | B2 * | 9/2015 | Halberthal | A61B 19/44 |
| 9,280,738 | B2 * | 3/2016 | Dor | G06K 19/07758 |
| 2006/0214791 | A1 | 9/2006 | Tethrake et al. | |
| 2006/0232407 | A1 | 10/2006 | Ballard | |
| 2008/0238677 | A1 * | 10/2008 | Blair | A61B 5/06 340/572.1 |
| 2009/0078762 | A1 * | 3/2009 | Forster | A01K 11/001 235/385 |
| 2011/0023343 | A1 * | 2/2011 | Turner | G09F 3/0292 40/662 |
| 2014/0048605 | A1 * | 2/2014 | Gatling | B23B 45/00 235/492 |
| 2014/0125482 | A1 * | 5/2014 | Rigsby | A61B 17/7001 340/539.13 |
| 2014/0159900 | A1 * | 6/2014 | Joseph | G08B 13/2417 340/572.1 |

FOREIGN PATENT DOCUMENTS

| | | | | |
|---|---|---|---|---|
| WO | 2014/1222239 | A1 | 8/2014 | |
| WO | WO 2014122239 | A1 * | 8/2014 | G06K 19/07728 |

* cited by examiner 100
110
120
130
140
150
160

100
130
120
232

INTERCHANGEABLE TAG AND ATTACHMENT

TECHNICAL FIELD

The present invention relates to the attachment of interchangeable identification tags to small objects and tools.

BACKGROUND

There are many environments in which multiple tools and disposables are used, including for example operation rooms, aircraft hangars, garages, or the like.

An operation room is a facility in which intrusive operations are performed on patients. Typically, multiple people participate in an operation, including a chief surgeon, sometimes an assistant surgeon, an anesthesiologist, a scrub nurse, and a circulating nurse. The participating personnel members use multiple surgical items, such as scalpels, forceps, and others, varying according to the surgery being, performed.

Intensive efforts are invested in keeping track of all surgical items and disposables, in order to make sure no item unintentionally remains inside the patients body. Therefore careful counting is performed before, during and after the operation.

Counting the surgical items is a tedious job and requires intensive resources, including mental resources, personnel time and down-time of the operating room. Counting the surgical items towards the end of an operation also increases the time the patients body is open with the associated risks.

In addition, counting is not always error-free, and in many cases surgical items end up being left within the patients body, causing severe damage and even death.

Another problem relates to the life cycle of surgical items. For example, reusable surgical items used in an operation have to be sanitized or sterilized prior to further usage. Other constraints may relate to maintenance operations required for the surgical items, for example, a blade may have to be sharpened after every predetermined number of operations in which it is used. In another example, surgical items that have been used in an operation performed on a patient with a contagious disease may require extra sterilization before further usage, or the like. Making sure that each surgical item is used and maintained properly also imposes expenses and requires resources, including record keeping and tracking, manual labor and the like.

In U.S. Pat. No. 8,193,938 to Halberthal et al dated Jun. 5, 2012 there is disclosed a computerized system and method for keeping track of tools, wherein each tool is uniquely identified. Identifying the tools is performed using a Radio Frequency (RF) identification transducer tag that is attached to the tools. The use of a computerized system improves the ability to track the tools and reduce system overhead.

Attaching identifying tags to surgical items imposes a number of challenges. The tag needs to adhere to the surgical item for the entire lifetime of the surgical item, the tag should not interfere with the use of the surgical item, the tag should be identifiable regardless of the orientation of the surgical item and even when surrounded by other surgical items.

Application Ser. No. 14/269,155 to Guy Dor et al dated May 4, 2014 the disclosure of which is incorporated herein by reference discloses construction of an identification tag and attaching it to a tool. Generally the attachment process is performed by laser welding to prevent damage to the tag from excess heating. The welding process generally requires that a skilled person perform the attachment process to prevent damage to the tag while being attached.

The current attaching process is time consuming and expensive. In an environment with many tools/surgical items a lot of skilled technicians may be required for attaching identification tags to the tools. Thus it is of interest to reduce the attaching time and simplify it so that even a non-skilled worker may quickly attach identification tags.

It should be noted that government regulatory authorities (e.g. the FDA) are in the process of introducing regulatory requirement requiring medical facilities to mark tools with unique device identifiers (UDI). Thus it is of interest to simplify the attachment process to reduce the overhead and risk of not being in compliance with the regulations.

SUMMARY

An aspect of an embodiment of the disclosure relates to an interchangeable tag for automatically identifying a tool/surgical item. The interchangeable tag includes a base with a small footprint for attaching the tag to the surgical item on one end of the base, and an identification head that is attached to the other end of the base. The identification head has a footprint that is larger than the footprint of the base. The identification head includes an identification circuit that accepts wireless communication queries and responds with identification information for identifying the surgical item. Additionally, the base is attached to the surgical item by a technological process that requires use of an attachment tool or technique by a skilled user and the identification head is attached to the base after attaching the base to the surgical item by a simple process that is performed without requiring an attachment tool. In an exemplary embodiment of the disclosure, the attachment tool required for the technological process heats the base to attach it to the surgical item. Optionally, to attach the base to the surgical item, the base is heated to a temperature that would damage the identification head if it were coupled to the base while attaching the base to the surgical item.

In an exemplary embodiment of the disclosure, the identification head is attached to the base by being screwed on or clicked on. Optionally, the connection is designed so that once they are connected they cannot be taken apart without breaking the attachment point with the base to secure the ability to track the surgical item.

In an exemplary embodiment of the disclosure, the base is designed so that the identification head will always be aligned with a plane that substantially coincides with the surgical item when connected (especially surgical items that are mainly planar e.g. a pair of scissors), so that the identification head won't stick out (e.g. an elongated identification head won't form an angle relative to the plane of the surgical item). Optionally, the base may have two stages one for attaching it to the surgical item and one for adjusting rotation of the identification head relative to the surgical item.

In some embodiments of the disclosure, surgical items are provided by the manufacturers with the base already embedded within the surgical item and/or attached to the surgical item so that a user in an organization merely needs to attach identification heads using a simple attachment process that can be performed by the user.

There is thus provided according to an exemplary embodiment of the disclosure, an interchangeable tag for attaching to an item for automatically identifying the item, comprising:

A base with a small footprint for attaching to the item at a first end of the base;

An identification head with a larger footprint that is attached to the item by said base at a second end of the base; wherein the identification head wirelessly accepts communication queries and transmits identification information related to the item; and Wherein the base is attached to the tool by a technological process that requires use of an attachment tool by a skilled user and the identification head is attached to the base after attaching it to the item by a simple process that is performed without requiring an attachment tool.

In an exemplary embodiment of the disclosure, the attachment tool required for the technological process heats the base to attach it to the item. In some embodiments of the disclosure, the base is pre-attached to the item by the item manufacturer.

In an exemplary embodiment of the disclosure, the attachment tool includes a mark to indicate how to align the attachment tool relative to the item so that the base is attached correctly to the item. Optionally, the base has a special shape and the attachment tool is configured to grasp the base in a specific way to match the special shape. In an exemplary embodiment of the disclosure, the base is attached to the item by a laser welding process. Optionally, the base is attached to the item by an ultra-sonic process. In an exemplary embodiment of the disclosure, the base includes a screw top for screwing on the identification head. Optionally, the screw top is configured to prevent unscrewing the identification head once it is screwed on. In an exemplary embodiment of the disclosure, the base includes a locking top that locks the identification head onto the base by pressing the identification head onto the locking top or by pressing and rotating the identification head onto the locking top. Optionally, the base is configured so that the identification head is aligned with the item after being attached to the base. In an exemplary embodiment of the disclosure, the base includes a fine tuning control to align the identification head after it is attached to the base. Optionally, the base includes a two stage element having an upper part and a lower part that are rotatable relative to each other to fine tune alignment of the identification head after it is attached to the base.

There is further provided according to an exemplary embodiment of the disclosure, an identification head for attaching to an item for automatically identifying the item, comprising:

A head with a large footprint that is attached to the item by a base having a smaller footprint; wherein the base is attached to the tool or embedded in the tool by the manufacturer;

Wherein the head wirelessly accepts communication queries and transmits identification information related to the item; and Wherein the head is attachable to the base by a simple process that is performed without requiring an attachment tool.

There is further provided according to an exemplary embodiment of the disclosure, a method of forming an interchangeable tag to identify an item, comprising:

Receiving a base with a small footprint and an identification head with a larger footprint; wherein the identification head is configured to wirelessly accept communication queries and transmits identification information related to the tool;

Attaching a first end of the base to a selected position on the item by a technological process that requires use of attachment tools by a skilled user;

Attaching a second end of the base to the identification head by a simple process that is performed without requiring attachment tools.

In an exemplary embodiment of the disclosure, the base includes a screw top for screwing on the identification head. Optionally, the screw top is configured to prevent unscrewing the identification head once it is screwed on. In an exemplary embodiment of the disclosure, the base includes a locking top that locks the identification head onto the base by pressing the identification head onto the locking top or by pressing and rotating the identification head onto the locking top. Optionally, the base is configured so that the identification head is aligned with the tool after being attached to the base. In an exemplary embodiment of the disclosure, the base includes a fine tuning control to align the identification head after it is attached to the base.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear. It should be noted that the elements or parts in the figures are not necessarily shown to scale and each elements or part may be larger or smaller than actually shown.

DETAILED DESCRIPTION

Figure 1:
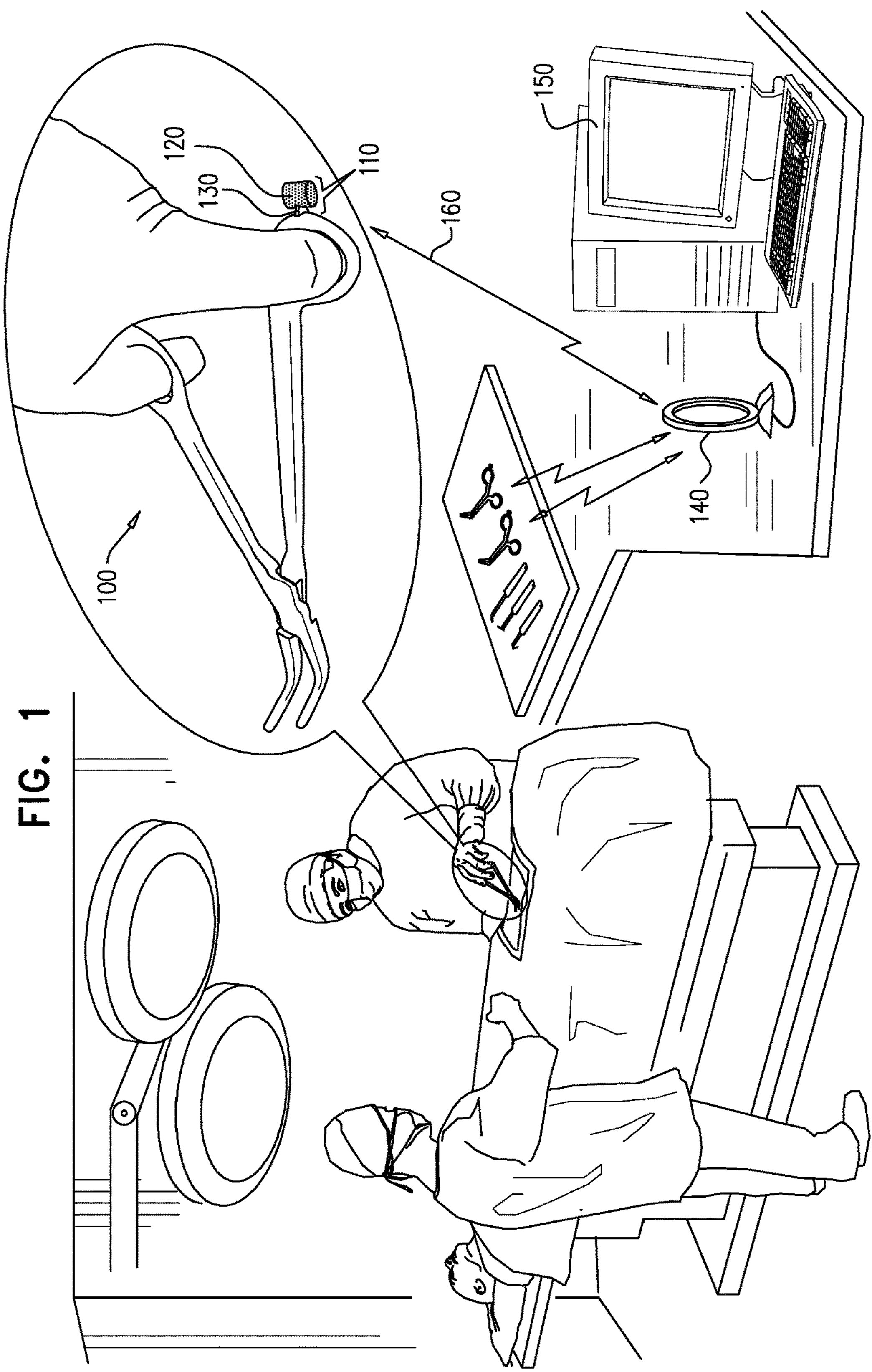
FIG. 1 is a schematic illustration of a surgical item with an interchangeable tag and an environment for using the surgical item, according to an exemplary embodiment of the disclosure.

FIG. 1 is a schematic illustration of a surgical item 100 with an interchangeable tag 110, according to an exemplary embodiment of the disclosure. Interchangeable tag 110 includes an identification head 120 that is connected to the surgical item 100 with a base 130 serving as an interface between the surgical item 100 and the identification head 120. In an exemplary embodiment of the disclosure, the base 130 has a small footprint relative to surgical item 100 and relative to identification head 120, so that it can be attached to surgical item 100 even if only a small area is available on the surgical item for attaching base 130. Optionally, the size of the footprint of base 130 is about 3 mm by 3 mm, 2 mm by 2 mm or less. In contrast identification head 120 has a footprint of about 5-9 mm by 3-6 mm or more thus covering an area of more than twice the size of the footprint of base 130. This enables use of larger identification head 120 with only a small attachment area on the surgical item 100. Additionally, a small attachment area allows quicker attachment (e.g. less heating). In a typical implementation, the actual attachment area (e.g. welding area) between base 130 and surgical item 100 is between 1-2 mm by 1-2 mm. Optionally, leaving a distance (by base 130) between the identification head 120 and the surgical item 100 prevents interference caused by the presence of surgical item 100, which is usually from solid metal from effecting identification head 120.

In an exemplary embodiment of the disclosure, base 130 is independent from identification head 120. Optionally, base 130 is attached to surgical item 100 first by a more technological attachment process that requires the use of tools by a trained user, for example laser welding, heating, ultra-sonic heating, adhesion, drilling or other processes that require more time (e.g. more than a few seconds). Afterwards identification head 120 is attached to the base 130 by a simple attachment process that can be performed in a few seconds and does not require much skill, for example screwing the identification head 120 onto the base 130 or pushing down and/or rotating the identification head 120 relative to base 130 until it reaches a locking position. Optionally, identification head 120 is locked relative to base 130 and can only be removed by extreme force that will break the lock of base 130.

In an exemplary embodiment of the disclosure, base 130 is made from the same or similar material as surgical item 100 or at least the same material at the point of attachment on the surgical item, for example if surgical item 100 is made from a metal the base 130 is also made from a metal (e.g. both from stainless steel, titanium etc.). Likewise if the surgical item is made from a polymer also the base may be made from a polymer. Optionally, this allows treating surgical item 100 with the identification head 120 in the same manner as before the attachment, for example sterilizing, heating and the like. In an exemplary embodiment of the disclosure, the same material may mean the same material family, for example both made from metal, both made from a polymer or both made from a similar metal although not identical.

In some embodiments of the disclosure, metal surgical items and metal bases will be attached using a laser welding process, whereas polymer surgical items and polymer bases will be attached using an ultra-sonic process, gluing, friction stir welding or any other suitable technology for binding base 130 to surgical item 100. Optionally, base 130 is attached using a process that heats the base 130 to temperatures that could damage identification head 120 (e.g. burn out electronic circuits therein), however since the base is attached separately by a simple attachment process no damage is inflicted on the identification head 120.

In an exemplary embodiment of the disclosure, identification head 120 includes an RFID tag that provides a unique identifier. Optionally, during use one or more antennas 140 are positioned in the vicinity of surgical item 100. The antennas are capable of reading the unique identifiers by communicating (160) with identification head 120 and transmitting an identity of the identified surgical item to a computer 150. Optionally, computer 150 includes a processor and memory and keeps track of the identity of the identified surgical item 100, the time of identifying, the location of the surgical item 100 (or identity of the antenna 140 that located the identification head 120). In an exemplary embodiment of the disclosure, based on the recorded information, computer 150 can keep track of the surgical items 100 as they are moved from one location to another.

Figure 2A:
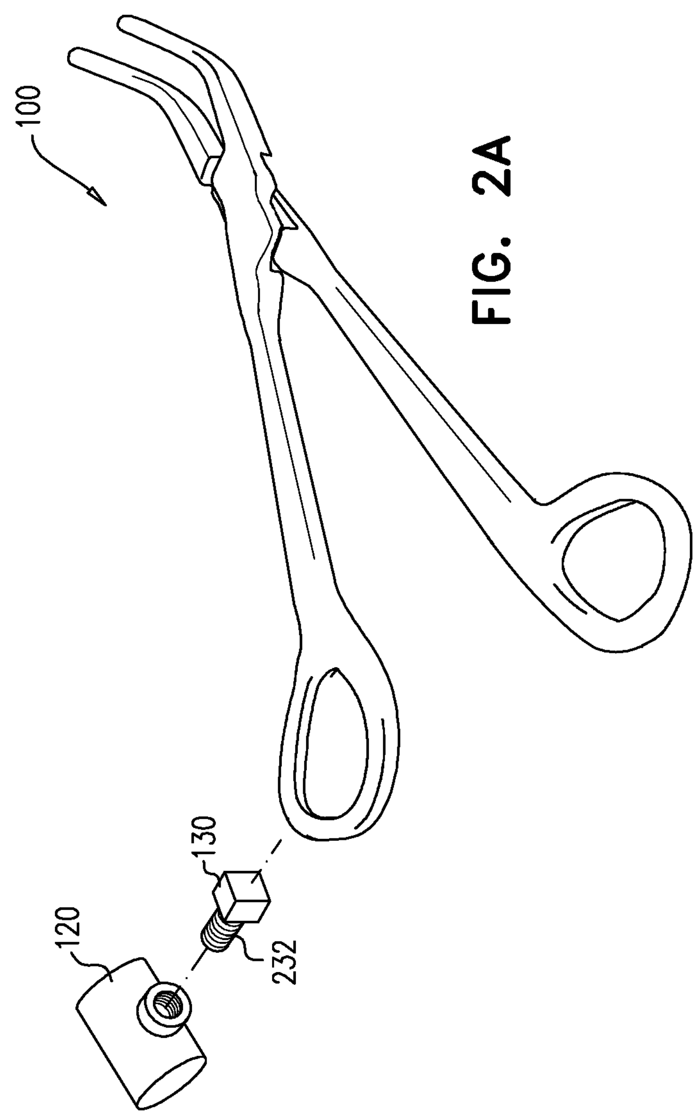
FIG. 2A is a schematic illustration of an exploded view of a surgical item with an interchangeable tag having an identification head and base, according to an exemplary embodiment of the disclosure.

FIG. 2A is a schematic illustration of an exploded view of a surgical item 100 with an interchangeable tag 110 having an identification head 120 and base 130, according to an exemplary embodiment of the disclosure. In some embodiments of the disclosure, base 130 includes a threaded screw top 232 for screwing on identification head 120. Optionally, identification head 120 is designed to serve as a screw on cap for base 130. In an exemplary embodiment of the disclosure, a drop of glue is placed on screw top 232 before attaching identification head 120 so that it will be permanently attached and cannot be removed without using extreme force. Alternatively or additionally, screw top 232 is designed with threads having breaks that prevent reopening the screw once it is closed. In some embodiments of the disclosure screw top serves as the male connector and identification head 120 serves as the female connector. Alternatively, it the roles may be reversed.

Figure 2B:
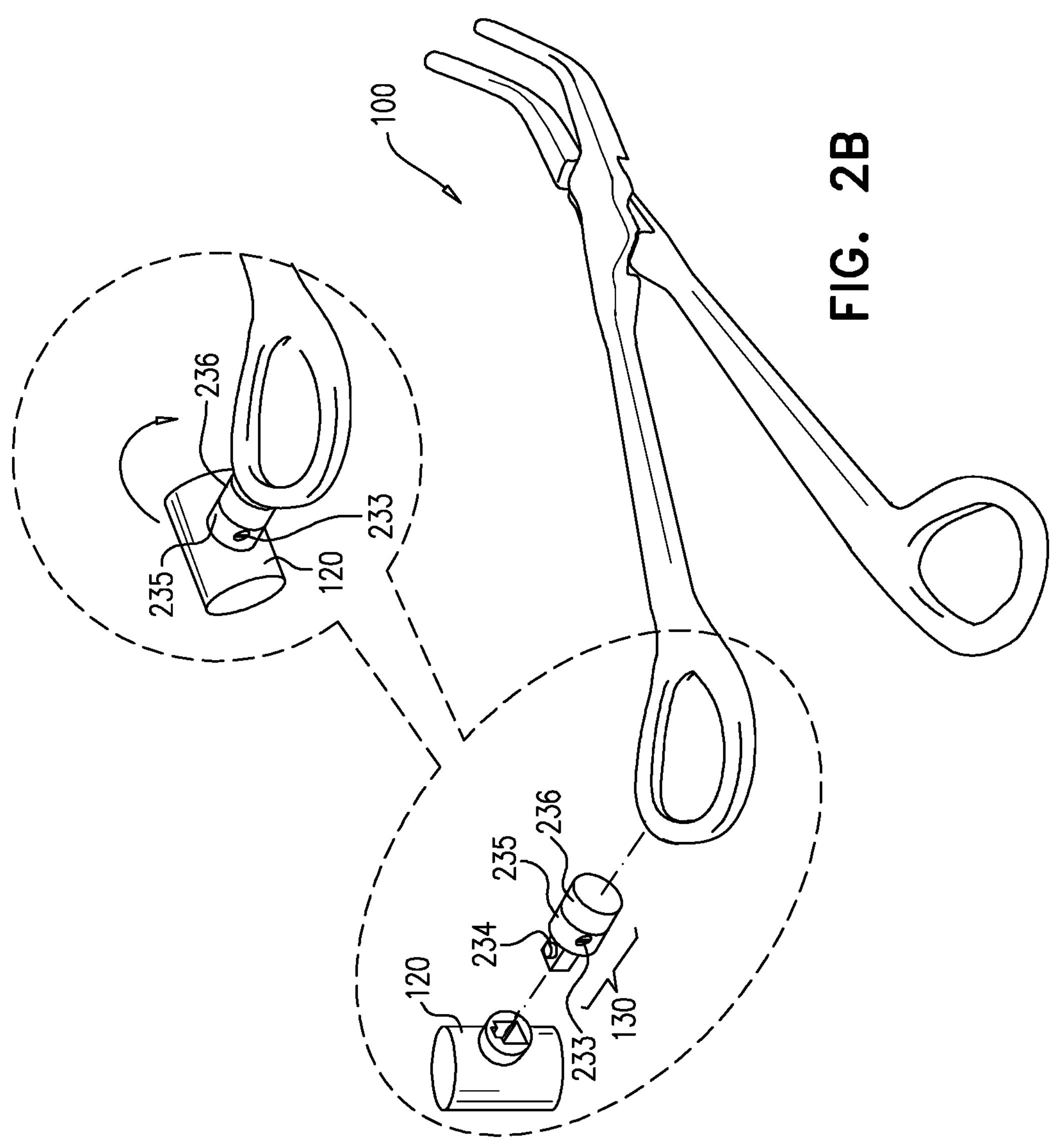
FIG. 2B is a schematic illustration of an exploded view of a surgical item with an alternative interchangeable tag having an identification head and base, according to an exemplary embodiment of the disclosure.

FIG. 2B is a schematic illustration of an exploded view of a surgical item 100 with an alternative interchangeable tag 110 having an identification head 120 and base 130, according to an exemplary embodiment of the disclosure. In some embodiments of the disclosure, base 130 includes a locking top 234 for locking on identification head 120. Optionally, identification head 120 is designed to serve as a cap that fits onto base 130 and is locked onto it by pushing down and/or rotating so that identification head 120 clicks into place and is locked so that it can only be remove by breaking the locking top 234. In some embodiments of the disclosure, base 130 includes a two (or more) stage element having an upper part 235 and a lower part 236 that may, rotate relative to each other for fine tuning the position of identification head 120. Optionally, an adjustment screw 233 may be used to lock upper part 235 and lower part 236 relative to each other so they don't rotate after adjusting the position of identification head 120.

Figure 2C:
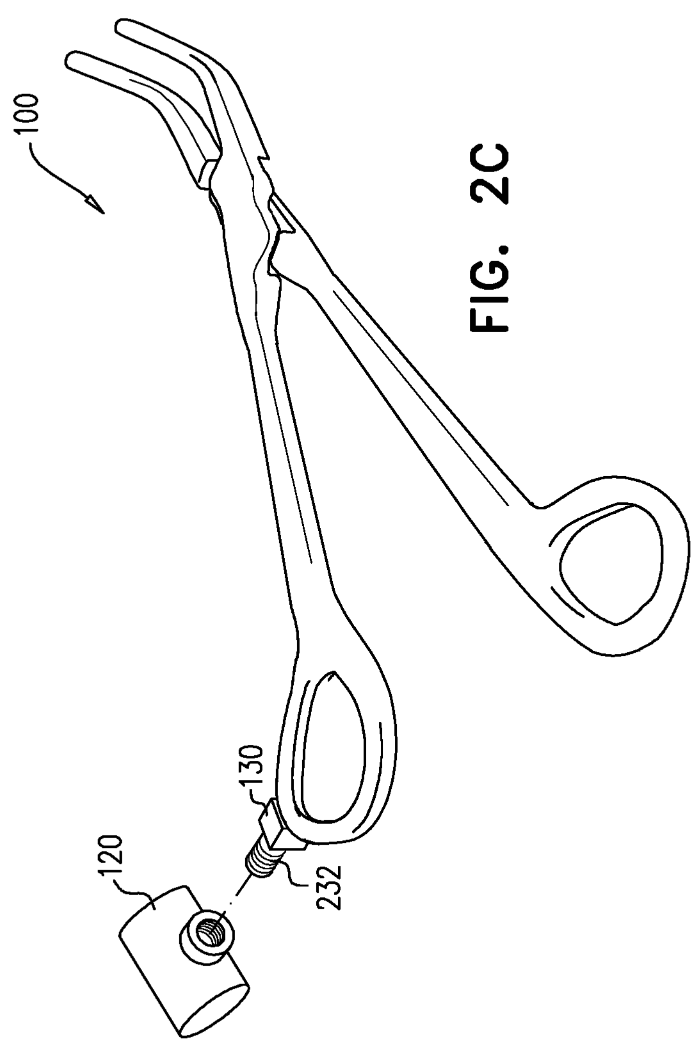
FIG. 2C is a schematic illustration of an exploded view of a surgical item with a further alternative interchangeable tag having a base that is pre-attached to the surgical item by the surgical item manufacturer, according to an exemplary embodiment of the disclosure.

FIG. 2C is a schematic illustration of an exploded view of a surgical item 100 with a further alternative interchangeable tag 110 having a base 130 that is pre-attached to the surgical item 100 by the surgical item manufacturer, according to an exemplary embodiment of the disclosure. Optionally, surgical item 100 is manufactured with base 130 already attached to it (as shown in FIG. 2C) so that the user only needs to attach an identification head 120 by a simple attachment process to finish installation of tag 110 for identifying surgical item 100. This simplifies installation for the user and reduces the cost to attach identification tags to surgical items 100. In an exemplary embodiment of the disclosure, in this case base 130 may have a screw top 232 as shown in FIG. 2A, a locking top 234 as shown in FIG. 2B or other types of simple attachment configurations for attaching with identification head 120 by a simple attachment process. In some embodiments of the disclosure, identification head 120 may have the protruding screw top or locking top and base 130 may have a matching opening for attaching to it.

Figure 2D:
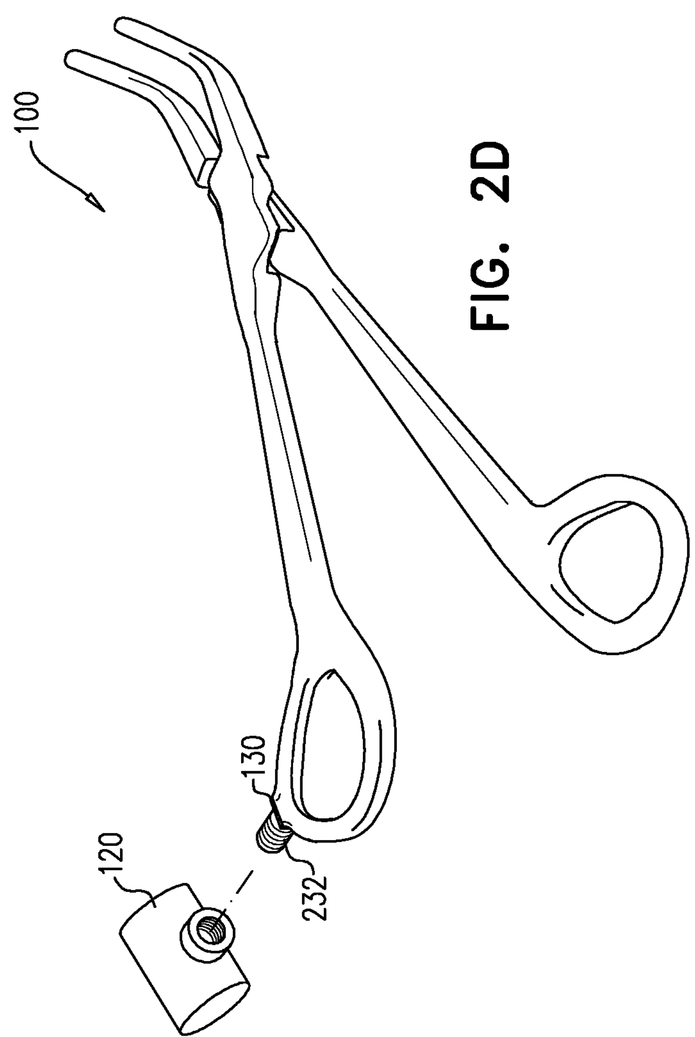
FIG. 2D is a schematic illustration of an exploded view of a surgical item with a further alternative interchangeable tag having a base that is embedded in the surgical item by the surgical item manufacturer, according to an exemplary embodiment of the disclosure.

FIG. 2D is a schematic illustration of an exploded view of a surgical item 100 with a further alternative interchangeable tag 110 having a base 130 that is embedded in the surgical item 100 by the surgical item manufacturer, according to an exemplary embodiment of the disclosure. Optionally a user only needs to attach identification head 120 by a simple attachment process to have the surgical item 100 equipped with an identification tag and ready for use. Optionally, removal of the identification head 120 will cause identification head 120 to be damaged so that it cannot be reused.

Figure 3:
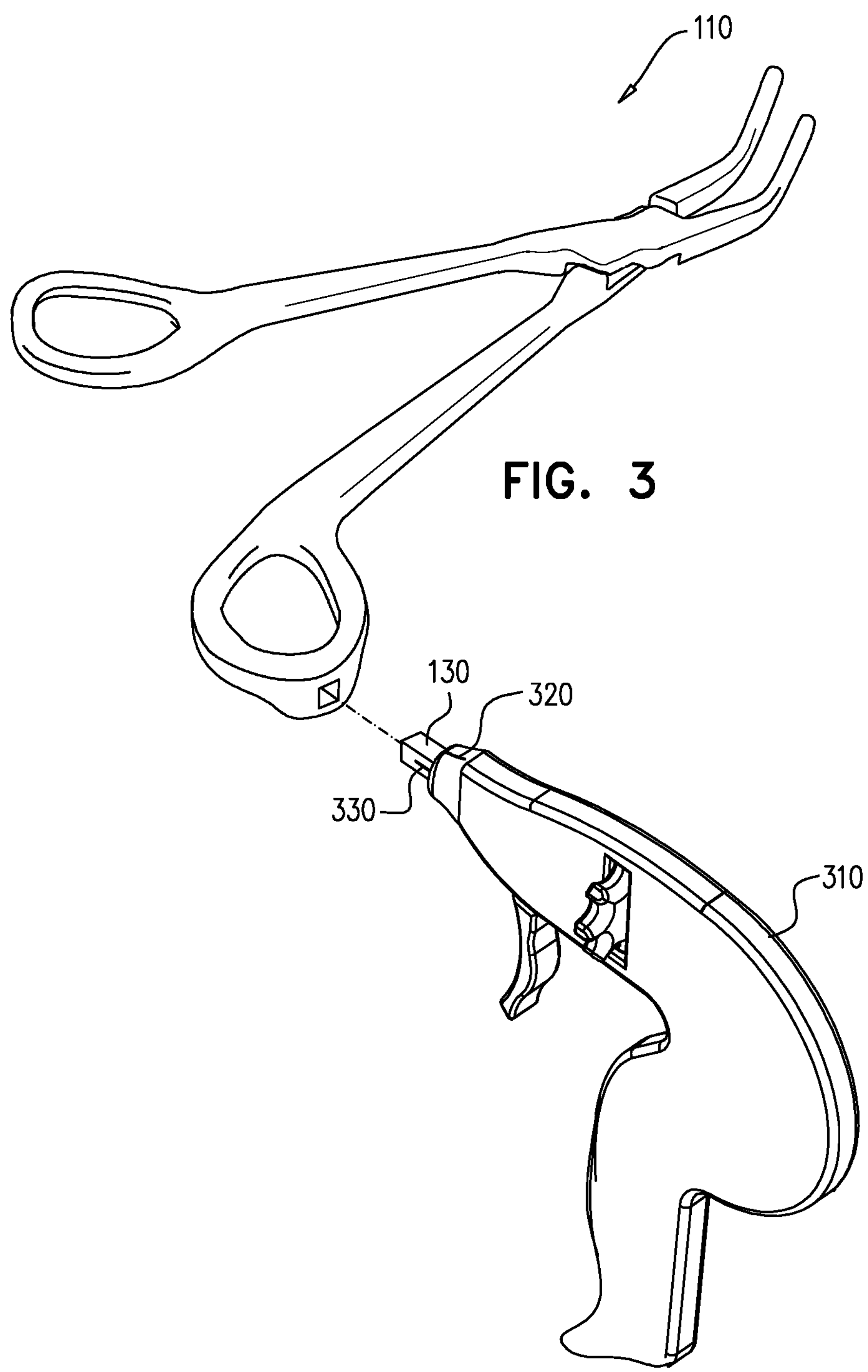
FIG. 3 is a schematic illustrations of an attachment toot for attaching a base, according to an exemplary embodiment of the disclosure.

FIG. 3 is a schematic illustrations of an attachment tool 310 for attaching a base 130, according to an exemplary embodiment of the disclosure. In some embodiments of the disclosure, a heating gun or other type of heating device is used to attach base 130 to surgical item 100 by heating the base 130 or surgical item 100 to a temperature that allows the base 130 to be permanently coupled to the surgical item 100 when placed in contact. Optionally, base 130 is grasped by the attachment tool 310 and heated to a high temperature. The user then places the base 130 in contact with the surgical item 100 and releases the base 130. By attaching base 130 separately from identification head 120 no damage is incurred to the identification head 120, which may have an electronic circuit or other heat sensitive elements embedded therein.

In some embodiments of the disclosure, attachment tool 310 includes a marking 320 or multiple markings 320 to provide an indication for the user as to the direction of aiming the attachment tool 310 when attaching base 130 to surgical item 100. In some embodiments of the disclosure, base 130 has a specific shape, for example a non-symmetrical footprint or with a groove 330 near the top of the base 130 or on a side of the base, for example along the height of base 130. Optionally, the special shape or groove defines the direction in which base 130 will be held by attachment tool 310, so that the user will know in which direction to aim attachment tool 310 when attaching base 130 to surgical item 100. In an exemplary embodiment of the disclosure, base 130 is designed so that identification head 120 will have a specific orientation when attached to base 130 after it is correctly attached to surgical item 100, for example so that an elongated axis of the tag 110 will be aligned with a plane in which the surgical item 100 is substantially situated so that the identification head 120 won't hinder use of the tool. Alternatively or additionally, identification head 120 or base 130 may allow fine tuning the orientation of screw top 232 or locking top 234, for example as described above (regarding FIG. 2B) by having a two or more stage base 130 having parts that are rotatable relative to each other (e.g. upper part 235 and lower part 236). Optionally, adjustment screw 233 serves as a fine tuning control to align identification head 120 with the plane of tool 100. Optionally, the fine tuning screw can be opened to rotate screw top 232 or locking top 234 relative to base 130.

Figure 4:
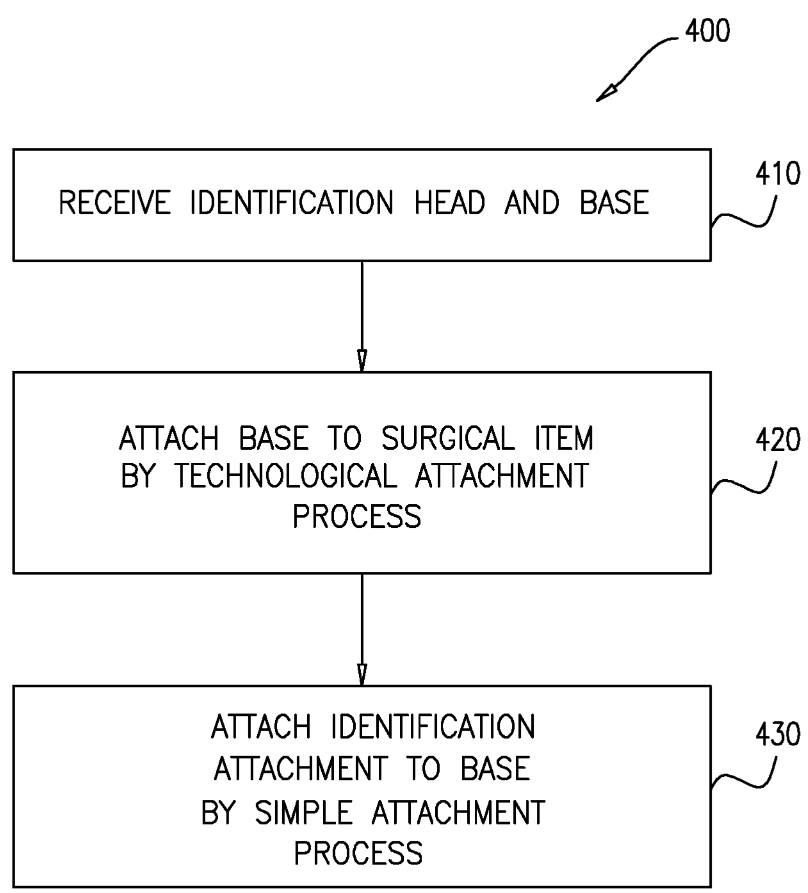
FIG. 4 is a flow diagram of a method of attaching a tag according to an exemplary embodiment of the disclosure.

FIG. 4 is a flow diagram 400 of a method of attaching a tag 110 to a surgical item 100 according to an exemplary embodiment of the disclosure. Optionally, the user receives (410) a base 130 and an identification head 120 with an RFID circuit inside for identifying surgical item 100. The user takes the base 130 for example with a screw top 232 or a locking top 234. The user attaches (420) the base 130 to surgical item 100 by a technological attachment process that requires attachment tools such as for performing laser welding, heat attachment or ultrasonic attachment. In an exemplary embodiment of the disclosure, after attaching the base 130 to surgical item 100 the user takes the identification head 120 and attaches (430) it to base 130 by a simple attachment process that does not require tools, for example by screwing on an identification head 120 or by pressing down identification head 120 and rotating it until it clicks into place. Optionally, the final orientation of identification head 120 is dictated by base 130 so that the user does not need to fine tune the final position, for example with identification head 120 lying in the same plane as the surgical item 100 and not protruding from the plane.

It should be noted that the above description describes mainly attaching tags to surgical items in a medical environment, however it should be noted that the disclosed apparatus and method are applicable also for other types of tools and items in other environments such as factories, garages, and maintenance facilities in general.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. An interchangeable tag for attaching to a surgical item for automatically identifying the surgical item, comprising:

a base with a footprint for attaching to the surgical item at a first end of the base;

an identification head with a footprint larger than the footprint of the base, which is attached to the surgical item by said base at a second end of the base; wherein the identification head wirelessly accepts communication queries and transmits identification information related to the identified surgical item; and wherein the base is attached to the surgical item by a first process that requires use of an attachment tool by a skilled user and the identification head is attached to the base after attaching the base to the surgical item by a second process that is performed without requiring an attachment tool;

wherein the second process attaches the identification head to the base preventing reopening without breaking the identification head or the base; and wherein the base includes a locking top that locks the identification head onto the base by pressing the identification head onto the locking top or by pressing and rotating the identification head onto the locking top.

2. The interchangeable tag according to claim 1, wherein the attachment tool required for the first process heats the base to attach it to the surgical item.

3. The interchangeable tag according to claim 1, wherein the base is pre-attached to the surgical item by the item manufacturer.

4. The interchangeable tag according to claim 1, wherein the attachment tool includes a mark to indicate how to align the attachment tool relative to the surgical item so that the base is attached correctly to the surgical item.

5. The interchangeable tag according to claim 1, wherein the base has a special shape and the attachment tool is configured to grasp the base in a specific way to match the special shape.

6. The interchangeable tag according to claim 1, wherein the base is attached to the surgical item by a laser welding process.

7. The interchangeable tag according to claim 1, wherein the base is attached to the surgical item by an ultra-sonic process.

8. The interchangeable tag according to claim 1, wherein the base is attached to the surgical item by adhesion.

9. The interchangeable tag according to claim 1, wherein the base is configured so that the identification head is aligned with the surgical item after being attached to the base.

10. The interchangeable tag according to claim 1, wherein the base includes a fine tuning control to align the identification head after it is attached to the base.

11. The interchangeable tag according to claim 1, wherein the base includes a two stage element having an upper part and a lower part that are rotatable relative to each other to fine tune alignment of the identification head after it is attached to the base.

12. An identification head for attaching to a surgical item for automatically identifying the surgical item, comprising:

a head with a footprint that is attached to the surgical item by a base having a smaller footprint than the footprint of the head; wherein the base is attached to the surgical item or embedded in the surgical item by the manufacturer;

wherein the head wirelessly accepts communication queries and transmits identification information related to the identified surgical item; and wherein the head is attachable to the base by a process that is performed without requiring an attachment tool;

wherein the process attaches the head to the base to prevent reopening without breaking the head or the base; and wherein the base includes a locking top that locks the head onto the base by pressing the head onto the locking top or by pressing and rotating the head onto the locking top.

13. A method of forming an interchangeable tag to identify a surgical item, comprising:

receiving a base with a footprint and an identification head with a footprint larger than the footprint of the base; wherein the identification head is configured to wirelessly accept communication queries and transmits identification information related to the identified surgical item;

attaching a first end of the base to a selected position on the surgical item by a first process that requires use of attachment tools by a skilled user;

attaching a second end of the base to the identification head by a second process that is performed without requiring attachment tools;

wherein the second process attaches the identification head to the base preventing reopening without breaking the identification head or the base; and wherein the base includes a locking top that locks the identification head onto the base by pressing the identification head onto the locking top or by pressing and rotating the identification head onto the locking top.

14. The method according to claim 13, wherein the base is configured so that the identification head is aligned with the tool after being attached to the base.

15. The method according to claim 13, wherein the base includes a fine tuning control to align the identification head after it is attached to the base.

* * * * *